(12) United States Patent
Gonopolskiy et al.

(10) Patent No.: US 8,558,178 B2
(45) Date of Patent: *Oct. 15, 2013

(54) PHYSIOLOGICAL SENSOR HAVING REDUCED SENSITIVITY TO INTERFERENCE

(75) Inventors: Oleg Gonopolskiy, West Bloomfield, MI (US); Arik Anderson, Birmingham, MI (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,717

(22) Filed: May 14, 2012

(65) Prior Publication Data

US 2012/0223213 A1 Sep. 6, 2012

Related U.S. Application Data

(63) Continuation of application No. 12/471,716, filed on May 26, 2009, now Pat. No. 8,188,433.

(51) Int. Cl.
*G01J 1/44* (2006.01)

(52) U.S. Cl.
USPC .................................... 250/338.1; 600/344

(58) Field of Classification Search
USPC .................................... 600/344; 250/338.1
See application file for complete search history.

(56) References Cited

U.S. PATENT DOCUMENTS

| | | |
|---|---|---|
| 5,159,929 A | 11/1992 | Morris |
| 6,023,541 A | 2/2000 | Merchant |
| 6,571,113 B1 | 5/2003 | Fein |
| 8,188,433 B2 * | 5/2012 | Gonopolskiy et al. ..... 250/338.1 |
| 2002/0026109 A1 | 2/2002 | Diab |
| 2008/0015424 A1 | 1/2008 | Bernreuter |

* cited by examiner

*Primary Examiner* — Constantine Hannaher
(74) *Attorney, Agent, or Firm* — Harness, Dickey & Pierce, PLC

(57) ABSTRACT

A physiological sensor having reduced sensitivity to interference includes a light source, a light detector in optical communication with the light source, and a sensor pad at least partially housing the light source and the light detector. The sensor pad is configured to be capacitively isolated from a patient. Moreover, the physiological sensor may be electrically connected to an amplifier having a signal ground and a monitor.

19 Claims, 2 Drawing Sheets

PHYSIOLOGICAL SENSOR HAVING REDUCED SENSITIVITY TO INTERFERENCE

CROSS-REFERENCE TO RELATED APPLICATIONS

This application is a continuation of U.S. application Ser. No. 12/471,716 filed on May 26, 2009, the contents of which are incorporated by reference herein in their entirety.

BACKGROUND

Physiological sensors are often used in medical applications to help doctors diagnose, monitor, and treat patients. Some physiological sensors use spectroscopy to provide valuable information about the patient's body tissue. Spectroscopy generally refers to the dispersion of light as it travels through a medium. A physiological sensor employing near-infrared spectroscopy may be used to detect characteristics of various body tissues by transmitting and receiving near-infrared light through the body tissue, and outputting a signal to a controller that provides valuable information about the body tissue. A doctor may use this information to diagnose, monitor, and treat the patient.

To measure the intensity of the light that travels inside the tissue, the near-infrared spectroscopy sensor may use one or more large area photodiodes mounted onto a flexible circuit board within a sensor pad. Because the photodiodes have a high equivalent resistance of the p-n junction, the sensor is very sensitive to the electromagnetic interference from other devices, such as electrosurgical equipment, electrocardiogram devices, or power supplies from medical or other electronic devices. One way to reduce the sensitivity of the near-infrared spectroscopy sensor to these other devices includes enclosing the photodiodes in a Faraday shield made from a copper mesh or plastic film covered by a transparent conductive material, such as iridium oxide. However, the Faraday shield is expensive, decreases the sensitivity of the photodiodes to the near-infrared light generated by the sensor, and reduces the flexibility of the sensor.

Accordingly, a sensor is needed that reduces or eliminates the effects of electronic devices without the added expense and/or decreased sensitivity in sensors employing the Faraday shield solution.

DETAILED DESCRIPTION

A physiological sensor includes a light source, a light detector, and a sensor pad that is capacitively isolated from a patient. When the sensor pad is placed on the patient, light from the light source travels through a portion of the patient's body and is at least partially received by the light detector. The light detector then outputs a signal to a signal ground that is indicative of oxygen saturation. However, electronic devices such as electrosurgical generators, electrocardiogram devices, power sources, or any other medical or non-medical devices near the sensor pad may interfere with the light received by the light detector. In particular, the electronic device may create a voltage potential between the patient and the sensor pad that generates an electromagnetic field that may be detected by the light detector. If detected, the electromagnetic field may affect the signal output by the light detector, causing false oxygen saturation readings. To remedy this, the sensitivity of the sensor may be reduced by capacitively isolating the sensor pad from the patient, which effectively reduces the voltage potential between the patient and the sensor pad and reduces the sensitivity of the sensor. Moreover, the sensitivity of the sensor may be further reduced by capacitively isolating the signal ground from the monitor.

Figure 1:
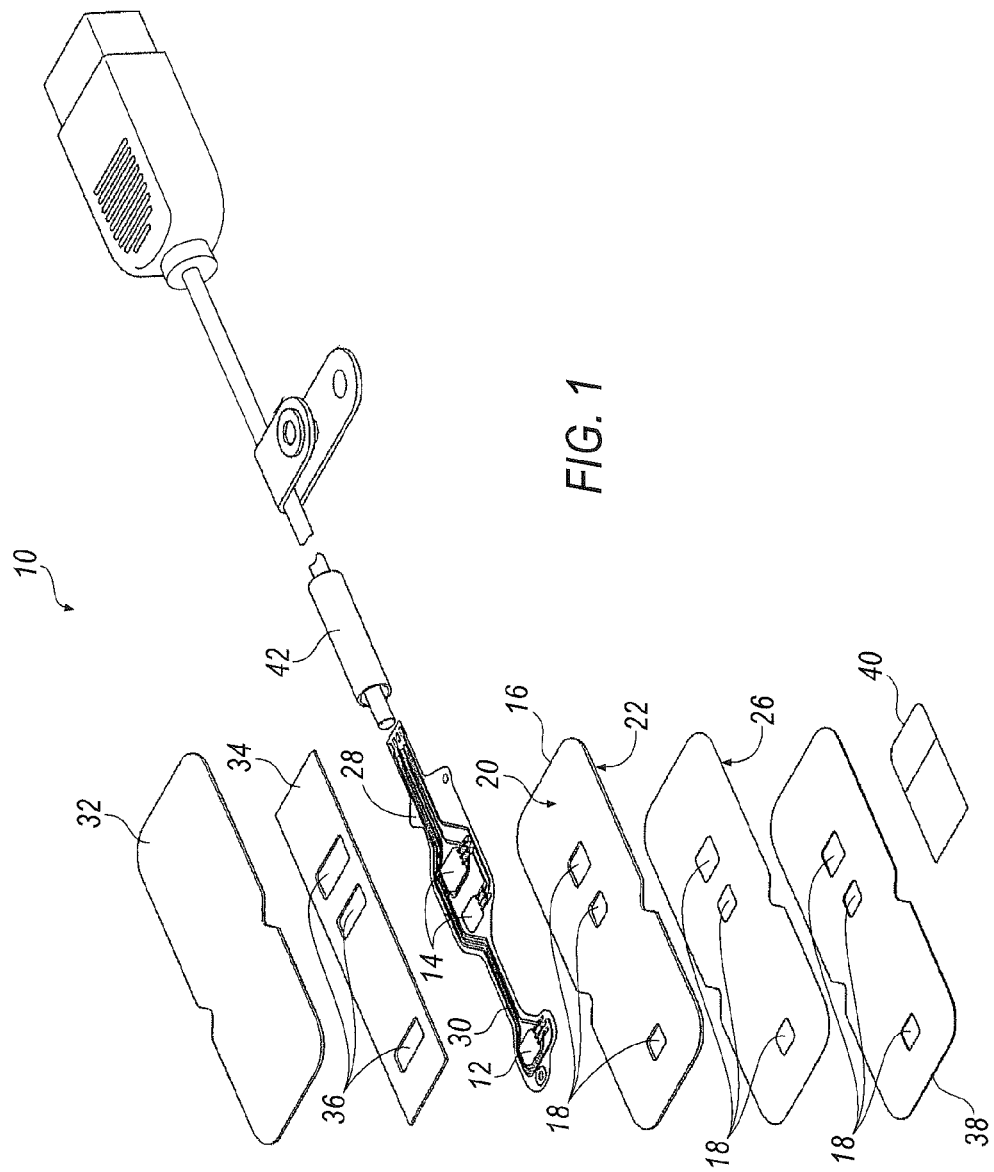
FIG. 1 is an assembly view of an exemplary physiological sensor configured to be capacitively isolated from a patient.

FIG. 1 is an assembly view of an exemplary physiological sensor 10 that is capacitively isolated from a patient on which the sensor 10 is placed. The sensor 10 includes a light source 12, such as a light emitting diode, that may be configured to generate light in a near-infrared region of the electromagnetic spectrum. A light detector 14, such as a photodiode, is in optical communication with the light source 12, and thus, may be configured to receive light in the same near-infrared region of the electromagnetic spectrum. This way, the sensor 10 may be configured be a pulse oximeter, tissue oximeter, or other device configured to detect oxygen saturation. Both the light source 12 and light detector 14 may be disposed on a sensor pad 16 such that the sensor pad 16 at least partially houses the light source 12 and the light detector 14. In one exemplary approach, the light source 12 may be disposed on a different sensor pad 16 than the light detector 14. Moreover, the sensor pad 16 may include any number of light sources 12 and/or light detectors 14. The sensor pad 16 includes openings 18 that allow light generated by the light source 12 to propagate through body tissue, as well as openings 18 that allow the light detector 14 to receive the light from the light source 14. To reduce the sensitivity of the sensor 10, the sensor pad 16 is capacitively isolated from the patient to a voltage potential between the patient and the sensor pad 16.

In one exemplary approach, a first surface 20 of the sensor pad 16 is at least partially coated with a conductive adhesive and a second surface 22 of the sensor pad 16 is at least partially coated with a pressure sensitive adhesive 26 that is not conductive to capacitively isolate the patient from the sensor pad 16. The second surface 22 of the sensor pad 16 is on the underside of the sensor pad 16 as illustrated in FIG. 1. Although coated on the second surface 22, the pressure sensitive adhesive 26 is illustrated in FIG. 1 as separate piece than the sensor pad 16 because it would otherwise not be viewable in FIG. 1. Moreover, the openings 18 for the light source 12 and the light detector 14 may further be defined by the second surface 22 and are thus illustrated in FIG. 1 as being further defined by the pressure sensitive adhesive 26.

It is appreciated that one or both of the first and second surfaces 20 and 22 may be completely coated with the conductive adhesive and the pressure sensitive adhesive 26, respectively. The conductive adhesive may be any conductive adhesive, such as ARCare-8001 manufactured by Adhesive Research Corporation. The pressure sensitive adhesive 26 may be any adhesive that will adhere to the patient's skin. When attached, the sensor pad 16 is arranged such that the conductive adhesive is spaced from the patient. The distance between the conductive adhesive and the patient's skin may affect the capacitance $C_p$ of the patient, discussed in further detail below (see FIG. 2). For example, the capacitance $C_p$ may be inversely related to the distance between the patient's skin and the conductive adhesive. In other words, as the distance between the conductive adhesive and the patient's skin increases, capacitance $C_p$ decreases, and vice versa. Therefore, the thickness of the sensor pad 16 may be designed to make the capacitance $C_p$ sufficiently small to reduce a field produced by the voltage difference between the patient and the sensor 10, yet large enough to capacitively isolate the patient from the sensor pad 16.

The capacitance $C_p$ may be similar to the capacitance of a parallel-plate capacitor the patient's body represents one plate and the conductive adhesive on the first surface 20 represents the other plate. The first surface 20 has an area A and is separated from the patient's body by a distance d. From this, capacitance $C_p$ is approximately equal to the following:

$$C_p = \epsilon_0 \epsilon_r A/d \qquad \text{(Equation 1)}$$

In Equation 1, $C_p$ is the capacitance in Farads, and as discussed above, A is the area of overlap of the first surface 20 and the patient's body measured in square meters, and d is the distance between the first surface 20 and the patient's body measured in meters. The value $\epsilon_r$ is the dielectric constant of the material between the plates, which may be approximately equal to 1. The value $\epsilon_0$ is the permittivity of free space where $\epsilon_0 = 8.854 \times 10^{-12}$ F/m. Using this equation, a 3 cm×1 cm sensor pad with a 1 mm gap between the patient's body and the first surface 20 would have a capacitance $C_p$ of approximately 3 pF. However, this value of $C_p$ is merely exemplary.

The sensor 10 itself may generate an electromagnetic field that may be received by and affect the light detectors 14. For example, the light source 12 and light detector 14 may be disposed on a printed circuit board 28 having traces 30. The spacing and configuration of the traces 30 may generate an electromagnetic field that interferes with the light detectors 14 in the same way a large voltage potential across the patient 44 and the sensor pad 16 may generate an electromagnetic field and affect the light detectors 14. To compensate for this type of electromagnetic field, the traces 30 on the printed circuit board 28 may be printed very close to one another to reduce the magnitude of any electromagnetic field generated therebetween. Moreover, the shape of the traces 30 may be such that there are few, if any, loops created. For example, the traces 30 may be configured to travel parallel to one another and in straight lines as much as possible, with few, if any, rounded edges. This will minimize a loop that may pick up a high frequency electromagnetic field from an interference current generated by an electrosurgical generator to the ground via the patient, as discussed in further detail below.

The sensor 10 may include other components, such as a light-blocking pad 32 disposed on the sensor pad 16 and over the printed circuit board 28 to reduce interference from ambient light, and a spacer 34 disposed between the light-blocking pad 32 and the printed circuit board 28. As illustrated, the spacer 34 may define openings 18 for each light source 12 and light detector 14. Further, the sensor 10 may include a shield 42 to protect signals transmitted from the light detector 14 to a signal ground 50 (see FIG. 2) from interference. When packaged, the pressure sensitive adhesive 26 may be covered with a liner 38, which may further define openings 36, and a tab 40 to allow removal of the liner 38 and expose the pressure sensitive adhesive 26 on the second surface 22 prior to placing the sensor 10 on the patient 44.

Figure 2:
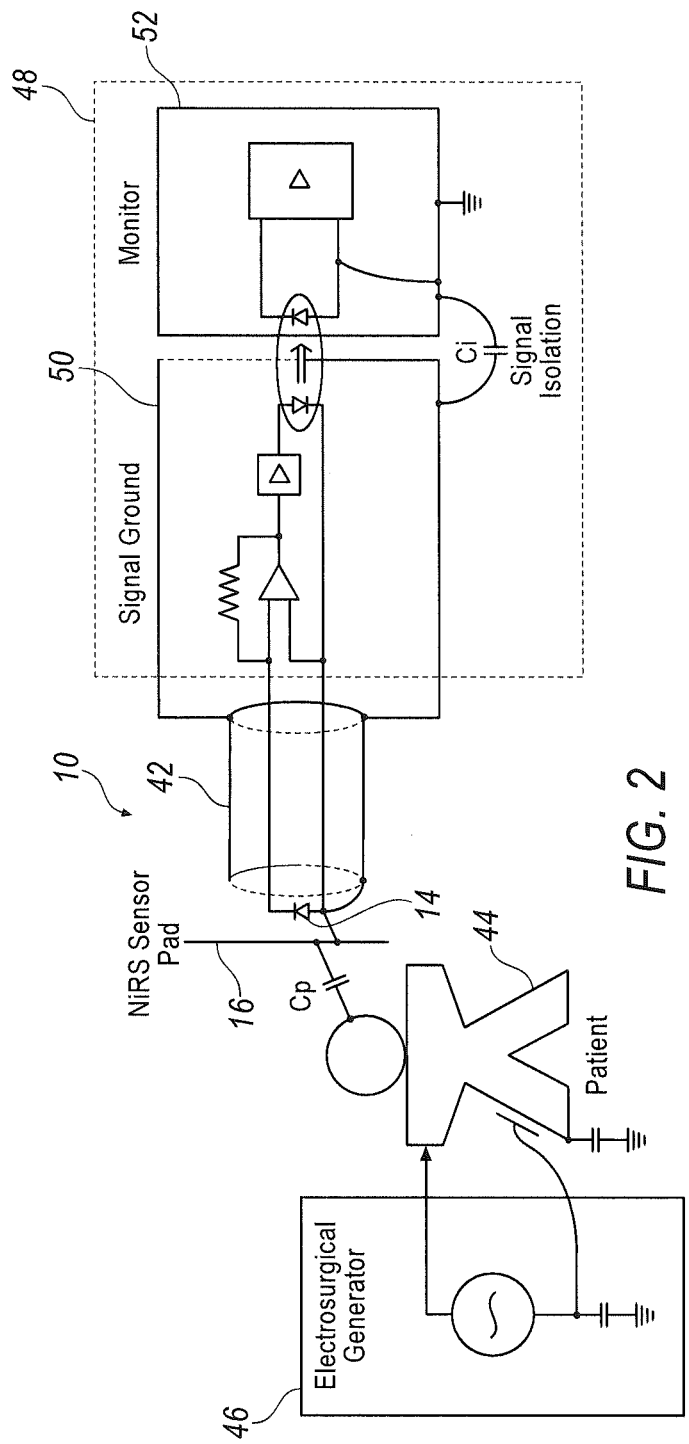
FIG. 2 is an exemplary circuit diagram illustrating an equivalent circuit of the physiological sensor capacitively isolated from the patient.

Referring now to FIG. 2, the physiological sensor 10 previously described may be used to detect oxygen saturation of a patient 44 without interference from an electronic device, such as an electrosurgical generator. Although illustrated as an electrosurgical generator, the electronic device 46 may be an electrocardiogram device, power supply, or any other medical or non-medical electronic device. The sensor 10 is in communication with an amplifier 48 having a signal ground 50 and a monitor 52. Namely, the light detector 14 outputs a current or voltage signal representative of oxygen saturation.

The amplifier 48 processes the signal and transmits the processed signal to the monitor 52 where the oxygen saturation may be graphically displayed to a user, such as a medical professional. The signal ground 50 may be connected to the sensor 10 via the conductive adhesive. In one exemplary approach, the conductive adhesive covers the entire first surface 20 of the sensor pad 16, and connects to the signal ground 50 via an exposed area of copper on the printed circuit board 28. This way, the signal ground 50 and the sensor 10 are at electrically the same potential, while capacitively isolated from the patient 44. Further, the shield 42 protects the signal transmitted from the light detector 14 to the signal ground 50 from interference.

The capacitance $C_p$ between the patient 44 and the sensor pad 16 absorbs changes in voltage between the sensor pad 16 and the patient 44 causing interference with the sensor 10, and in particular, an electromagnetic field received by the light detectors 14. The changes in voltage potential may be caused by an electronic device 46 used with the patient 44 as well as various physical characteristics of the patient 44, such as the patient's height, weight, etc, may cause these changes in voltage.

To further reduce interference, the signal ground 50 may be capacitively isolated from the monitor 52, represented in FIG. 2 as a signal isolation capacitance C. The isolation capacitance $C_i$ includes a parasitic capacitance between components of the monitor 52 and amplifier 48, a capacitance between an octo-coupler and a capacitance between primary and secondary windings of an isolation transformer providing electrical power to the amplifier 48 and sensor 10. In one exemplary approach, the capacitance $C_p$ between the patient 44 and the sensor pad 16 is greater than the signal isolation capacitance $C_i$, creating a voltage divider that decreases the electrical potential between the patient 44 and the light source 12. For example, the capacitance $C_p$ between the signal ground 50 and the monitor 52 may be 0.1 pF to 1.0 pF, and the capacitance $C_p$ between the patient 44 and the sensor pad 16 is greater than that. The signal isolation capacitance $C_i$ may be tuned relative to the capacitance $C_p$ between the patient 44 and the sensor pad 16 to control the reduction of interference.

The above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

We claim:

1. A sensor comprising:
   a sensor pad;
   a conductive material disposed on the sensor pad;
   a printed circuit board disposed on the conductive material, the printed circuit board including a light source configured to generate light and a light detector configured to receive light generated by the light source,
   wherein the sensor pad has a thickness that capacitively isolates the conductive material from a patient.

2. The sensor of claim 1, wherein a capacitance of the conductive material relative to the patient is inversely proportional to a distance between the conductive material and the patient and the distance is based on the thickness of the sensor pad.

3. The sensor of claim 2, wherein the capacitance between the conductive material and the patient is defined as: $C_p = \in_0 \in_r A/d$, wherein $C_p$ is the capacitance in Farads, A is an area of the sensor pad disposed on the patient, d is a distance between the conductive material and the patient, $\in_r$ is a dielectric constant between the conductive material and the patient, and $\in_0$ is a permittivity of free space.

4. The sensor of claim 3, wherein the dielectric constant between the conductive material and the patient is greater than 1.

5. The sensor of claim 1, wherein the conductive material is electrically connected to the printed circuit board.

6. The sensor of claim 5, wherein the conductive material and the printed circuit board are electrically grounded.

7. The sensor of claim 1, wherein the printed circuit board includes traces configured to minimize an electromagnetic field generated between the traces.

8. The sensor of claim 1, further comprising a light-blocking pad disposed on the sensor pad and configured to at least partially limit ambient light received by the light detector.

9. A system comprising:
   an amplifier configured to receive signals representing physiological information, wherein the amplifier includes a monitor configured to graphically display the physiological information represented by the received signals; and
   a sensor having a sensor pad, a conductive material disposed on the sensor pad, and a printed circuit board disposed on the conductive material, the printed circuit board including a light source configured to generate light and a light detector configured to receive light generated by the light source, wherein the sensor pad has a thickness that capacitively isolates the conductive material from a patient.

10. The system of claim 9, wherein a capacitance of the conductive material relative to the patient is inversely proportional to a distance between the conductive material and the patient and the distance is based on the thickness of the sensor pad.

11. The system of claim 10, wherein the capacitance between the conductive material and the patient is defined as: $C_p = \in_0 \in_r A/d$, wherein $C_p$ is the capacitance in Farads, A is an area of the sensor pad disposed on the patient, d is a distance between the conductive material and the patient, $\in_r$ is a dielectric constant between the conductive material and the patient, and $\in_0$ is a permittivity of free space.

12. The system of claim 9, wherein the sensor pad is capacitively isolated from the monitor.

13. The system of claim 9, wherein the conductive material is electrically connected to the printed circuit board.

14. The system of claim 13, wherein the conductive material and the printed circuit board are electrically grounded.

15. The system of claim 9, wherein the printed circuit board includes traces configured to minimize an electromagnetic field generated between the traces.

16. The system of claim 9, wherein the sensor includes a light-blocking pad disposed on the sensor pad, wherein the light-blocking pad is configured to at least partially limit ambient light received by the light detector.

17. The system of claim 9, further comprising a shield electrically disposed between the sensor and the amplifier.

18. The system of claim 9, wherein the amplifier includes a signal ground electrically connected to the sensor and capacitively isolated from the monitor.

19. A sensor comprising:
   a sensor pad;
   a conductive material disposed on the sensor pad;
   a printed circuit board disposed on the conductive material, the printed circuit board including a light source configured to generate light and a light detector configured to receive light generated by the light source,
   wherein the sensor pad has a thickness that capacitively isolates the conductive material from a patient and wherein a distance between the conductive material and the patient is based on the thickness of the sensor pad, and
   wherein a capacitance of the conductive material relative to the patient is defined as: $C_p = \in_0 \in_r A/d$, wherein $C_p$ is the capacitance in Farads, A is an area of the sensor pad disposed on the patient, d is a distance between the conductive material and the patient, $\in_r$ is a dielectric constant between the conductive material and the patient, and $\in_0$ is a permittivity of free space.

* * * * *